United States Patent [19]

Brazdil et al.

[11] 4,148,757

[45] Apr. 10, 1979

[54] PROCESS FOR FORMING MULTI-COMPONENT OXIDE COMPLEX CATALYSTS

[75] Inventors: James F. Brazdil, Bedford; Dev D. Suresh, Macedonia; Robert K. Grasselli, Chagrin Falls, all of Ohio

[73] Assignee: The Standard Oil Company, Cleveland, Ohio

[21] Appl. No.: 823,319

[22] Filed: Aug. 10, 1977

[51] Int. Cl.$^2$ .................. B01J 23/14; B01J 23/18; B01J 23/28; B01J 23/30
[52] U.S. Cl. .................. 252/432; 252/437; 252/439; 252/456; 252/458; 252/462; 252/465; 252/467; 252/468; 252/469; 252/470; 260/465.3; 260/604 R

[58] Field of Search .............. 252/432, 437, 439, 462, 252/465, 467, 468, 469, 470, 456, 458; 260/465.3

[56] References Cited

U.S. PATENT DOCUMENTS

| | | | |
|---|---|---|---|
| 3,895,051 | 7/1975 | Umemura et al. | 252/467 X |
| 3,951,861 | 4/1976 | Shiraishi et al. | 252/467 X |
| 4,040,978 | 8/1977 | Li | 252/437 |

*Primary Examiner*—W. J. Shine
*Attorney, Agent, or Firm*—John E. Miller, Jr.; Herbert D. Knudsen; Larry W. Evans

[57] ABSTRACT

Multicomponent complex oxide catalysts based on bismuth molybdate, for example, are made by a technique in which the bismuth molybdate portion of the catalyst is preformed prior to combining with the remaining elements of the catalyst.

13 Claims, No Drawings

PROCESS FOR FORMING MULTI-COMPONENT OXIDE COMPLEX CATALYSTS

BACKGROUND OF THE INVENTION

The present invention relates to catalysts useful in the oxidation and/or ammoxidation of olefins. More specifically, the present invention relates to a novel process for producing oxidation and/or ammoxidation catalysts having superior properties.

It is well known that olefins can be oxidized to oxygenated hydrocarbons such as unsaturated aldehydes and acids, for example, acrolein and methacrolein, and acrylic and methacrylic acids. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant and for the production of methacrolein and methacrylonitrile, isobutylene is the generally used olefin reactant.

Many different catalysts have been disclosed as useful in the oxidation and ammoxidation of olefins. For example, see U.S. Pat. Nos. 3,882,159 and 3,746,657. Also see commonly assigned application Ser. No. 748,609, filed Dec. 7, 1976, the disclosure of which is incorporated herein by reference. As will be noted, catalysts based on bismuth and molybdenum, i.e. bismuth molybdate catalysts, promoted with various additional elements such as iron, cobalt, nickel, potassium, phosphorus, chromium, manganese and the like show special utility for these reactions.

Bismuth molybdate catalyst have been prepared in the past by a number of different techniques. For example, Example III of U.S. Pat. No. 3,746,657 shows a preparation method comprising forming a mixture of potassium hydroxide, ammonium molybdate and silica, adding to the mixture phosphoric acid, solutions in nitric acid of the nitrates of cobalt, iron, nickel and bismuth, and more silica to form a slurry, then spray drying and calcining to form the catalyst. Application Ser. No. 748,609 discloses a catalyst preparation technique in which an aqueous solution of cobalt nitrate and nickel nitrate, an aqueous solution of potassium nitrate and iron nitrate, an aqueous nitric acid solution of bismuth nitrate and a silica sol are added in order to an aqueous solution of ammonium heptamolybdate and phosphoric acid, and the composition so obtained sprayed dried and calcined to form the catalyst. This application discloses another catalyst proparation technique in which an aqueous nitric acid solution of ferric nitrate and bismuth nitrate is added to a previously formed aqueous slurry containing ammonium heptamolybdate, phosphoric acid, arsenic acid, silica sol, nickel nitrate and cobalt nitrate, the composition so obtained heated until a gel forms, and the gel dried and calcined to produce the ultimate catalyst.

Each of the known techniques of catalyst preparation has relative advantages and disadvantages. Also, there has been some indication that the catalytic properties of the ultimate catalysts produced can be improved if specific catalysts preparation techniques are followed. As yet, however, there is no known catalyst preparation technique which is both simple and easy to perform and capable of enhancing the catalytic properties of the ultimate catalyst.

Accordingly, it is an object of the present invention to provide a catalyst preparation technique especially suited for preparing bismuth molybdate type catalysts which is both simple and easy to perform as well as capable of enhancing the catalytic properties of the catalyst produced.

SUMMARY OF THE INVENTION

This and other objects are accomplished by the present invention in accordance with which a bismuth molybdate-catalyst is prepared by a procedure in which bismuth molybdate is separately produced and then the performed bismuth molybdate is combined with the other elements of the catalyst to form the ultimate catalyst product. In accordance with the present invention, it has been discovered that the catalytic activity of various types of multi-component oxidation and ammoxidation catalysts can be significantly enhanced if the key catalytic phase (for example, bismuth molybdate in the case of a bismuth molybdate-type catalyst) is preformed prior to combining it with the remaining elements of the desired catalyst.

DETAILED DESCRIPTION

The inventive catalyst preparation technique is applicable to a wide variety of different types of catalysts, the compositions of which are generally well known. Such catalysts can be described by the following general formula:

wherein:
M = Bi, Te, Sb, Sn, and/or Cu
N = Mo and/or W
A = alkali, Tl, and/or Sm
C = Ni, Co, Mn, Mg, Be, Ca, Sr, Ba, Zn, Cd and/or Hg
D = Fe, Cr, Ce, and/or V
E = P, As, B, Sb
F = rare earth, Ti, Zr, Nb, Ta, Re, Ru, Rh Ag, Au, Al, Ga, In, Si, Ge, Pb, Th, and/or U, and further wherein
a = 0–4
b = 0–20
c = 0.01–20
d = 0–4
e = 0–8
f = 8–16
m = 0.01–10
n = 0.1–30, and
x and y are numbers such that the valence requirements of the other elements for oxygen in the key catalytic phase and the host-catalyst phase, respectively, are satisfied; and the ratio q/p is 0.1 to 10, preferably 0.5–4.

In such catalysts, the portion denoted by

is denoted as the key catalytic phase, while the portion of the catalyst defined by $[A_aC_bD_cE_dF_eMo_fO_y]$ is the host-, promoter-, and/or co-catalyst phase (hereinafter referred to as the host-catalyst phase).

In this connection, although the foregoing catalyst description indicates that the catalysts produced by the inventive process are composed of two phases, namely a key catalytic phase and a host-catalyst phase, this terminology is used for descriptive purposes only. Oxide catalysts of the type described are well known in the art and normally take the form of some type of oxide complex, the specific structure of which is extremely complex and not completely understood. The catalysts produced by the inventive process are of a similar nature. More specifically they are not composed of a simple mixture of the key and host-catalyst phases but rather a complex composition in which the key and host-catalyst phases interact with one another and which may be composed of one or more phases.

In the foregoing formula, M is preferably Bi and N is Mo. Of these catalysts, those containing nickel, cobalt and iron and optionally phosphorous or antimony, are preferred, and of these catalysts those containing an alkali metal, most preferably potassium, rubidium and/or cesium, are especially preferred. Also, if the catalyst contains a Group IIA or IIB metal, it is preferably selected from the Group consisting of Mg, Cd and Zn.

An important feature of the present invention as indicated above is that the key catalytic phase of the catalyst, for example bismuth molybdate, is preformed prior to combining with the other elements of the catalyst. The key catalytic phase can be made in accordance with any conventional technique. For example, bismuth molybdate can be conveniently prepared by adding ammonium heptamolybdate, $(NH_4)_6Mo_7O_{24}\cdot 4H_2O$, to an aqueous solution of bismuth nitrate, preferably in a nitric solution, and then adjusting the pH to form a precipitate of bismuth molybdate. Alternately, other bismuth salts having decomposable anions can be employed. For example, acetate, triphenyl, citrate and so forth salts of bismuth can be employed to form bismuth molybdate. Similarly, decomposable salts of the other M elements can be used to supply the M component of the key catalytic phase, while ammonium tungstate, tungstic acid and the like can be used to supply tungsten, and ammonium molybdate and $MoO_3$ in aqueous $NH_4OH$ can be used to supply molybdenum to both the hg and host-catalyst phases.

Still another technique for forming the key catalytic phase is by known metallurgical techniques, for example, by reacting bismuth oxide and molybdenum oxide together in the solid phase.

Preparation of molybdates and/or tungstates of the various elements M listed in the foregoing formula are well known in the art. Thus those skilled in the art should be able to produce the pre-formed catalytic phase of the catalyst of the inventive process with no difficulty.

In producing the key catalytic phase of the objective catalysts, the amount of M and N components combined together is, of course, dependent upon the ultimate composition of the objective catalyst as well as the amount of N element in the co-catalyst phase. Within this framework, however, it is desirable that the ratio M/N in forming the key catalytic phase be maintained within the range of 1:9 to 9:1, preferably 2:1 to 1:3 and most preferably 2:1 to 2:3. When producing bismuth molybdate as the key catalytic phase, it is especially preferred that the M/N ratio be 2:1 to 1:3 and most preferably 2:1 to 2:3.

The remaining elements of the objective catalyst which form the co-catalyst phase can be combined with the preformed key catalytic phase in any manner. For example, a single solution or slurry containing all of the ingredients of the co-catalyst phase can be added to the pre-formed key catalytic phase and the composition so obtained dried and calcined to produce the objective catalyst. Alternatively, one or more of the elements in the co-catalyst phase can also be pre-formed into a molybdate and/or tungstate prior to admixing with the pre-formed key catalytic phase. For example, the chromium content of the co-catalyst phase can be formed into chromium molybdate (in the case of a molybdate catalyst) prior to addition to the key catalytic phase. Since, however, it is desirable that the inventive catalyst preparation be as simple as possible, it is preferred to form the co-catalyst phase in a single operation. In any event, it is necessary in order to keep the inventive process simple that none of the Group VIII elements in the catalyst, if any, is individually pre-formed into a molybdate or tungstate since to do so would make the preparation procedure unduly and unnecessarily complex.

As indicated above, the co-catalyst phase can be combined with the key catalytic phase in the form of a solution or slurry, the solution or slurry preferably being aqueous. If a co-catalyst phase in the form of a solution is employed, the solution is added to the key catalytic phase (either in the form of a solid or a slurry) and the composition so obtained heated to drying. In accordance with well known chemical phenomena, heating, pH adjustment or other appropriate treatment of the aqueous composition causes precipitation of the components dissolved in the liquid phase of the slurry, thereby producing a precipitate which together with the pre-formed key catalytic phase forms a pre-catalyst of appropriate composition. Drying and calcination of the pre-catalyst in accordance with conventional procedures causes decomposition of decomposable anions and cations thereby yielding an activated catalyst of the objective composition.

If the co-catalyst phase is in the form of a slurry rather than a solution, this slurry is admixed with the key catalytic phase (either in the form of a slurry or a solid) and the composition so obtained dried and calcined in the same manner as discussed above to produce a catalyst of the objective composition.

In a similar manner, an aqueous solution or slurry containing less than all of the elements in the co-catalyst phase can be added to the key catalytic phase. In such a situation, of course, additional one or more solutions or slurries containing the remaining elements constituting the co-catalyst phase must also be added to the key catalytic phase to produce the objective catalyst. In any event, the manner in which the elements of the co-catalyst phase are combined with the key catalytic phase is unimportant so long as none of the Group VIII elements in the catalyst, if any, are preformed into molybdates and/or tungstates individually. However, it is preferable that precipitation (during preparation of both the key- and host-catalyst phases) be accomplished in such a way that the production of molybdates and/or tungstates is maximized and the production of oxides is minimized. This can be accomplished by suitable adjustment of pH.

The starting materials used to supply particular elements for forming the co-catalyst phase can be any materials conventionally employed in the manufacture of oxidation catalysts. Normally, decomposable salts which will yield the desired elements upon heating to elevated temperatures are employed, although oxides and even free acids can be employed as can salts in which with the anion and cation contribute elements to the ultimate catalyst such as $KH_2PO_4$. For example, nitrate, acetate, triphenyl and citrate salts of the elements in question can be employed as can phosphoric acid, antimony oxide and chromium trioxide. Nitrate salts find particular applicability in prior art processes and are especially useful in the inventive process.

Techniques for forming oxide complex catalysts containing a wide variety of different elements and based on molybdates or tungstates are well known in the art, and those skilled in the art should have no difficulty in determining how to incorporate a particular element into the catalyst of the present invention. So long as the key catalytic phase of the objective catalyst is preformed and no Group VIII element is individually preformed, the objective catalyst produced will have excellent catalytic activity even though prepared by a very simple and straight forward procedure.

In accordance with a preferred embodiment of the present invention, the objective catalyst is most simply made by combining together an aqueous slurry of the key catalytic phase and an aqueous slurry of the host-catalyst phase, drying the composition so obtained to yield a solid pre-catalyst precipitate and calcining the precipitate to form a catalyst of the objective composition. The key catalytic phase aqueous slurry is preferably made by co-precipitation techniques using decomposable salts (preferably nitrates and ammonium salts), and the aqueous slurry of the host-catalyst phase is similarly made by co-precipitation with decomposable salts (preferably nitrates and ammonium salts) and if desired oxides and free acids.

In another very simple way of carrying out the inventive process the starting materials used for supplying the elements of the host-catalyst phase (e.g. nitrate salts, free acids, oxides, etc.) can be individually added (either in the form of a solid or a slurry) to an aqueous slurry of the key catalytic phase, and the precipitate obtained on drying calcined in the usual manner.

A significant feature of the inventive process is that the key catalytic phase of the objective catalyst once pre-formed can be combined in essentially any form with the remaining ingredients of the catalyst. For example, the key catalytic phase, which is normally derived in the form of an aqueous slurry, can be combined with the other elements of the catalyst still in the form of this aqueous slurry. In other words, no filtering of the key catalytic phase slurry to remove the mother liquor therefrom is necessary in accordance with the present invention. Indeed, filtering is undesirable since it complicates the preparation procedure. Alternately, the pre-formed key catalytic phase can be separated from the mother liquor, as by filtration, and combined with the other ingredients of the catalyst in this form. Furthermore, if desired, the key catalytic phase can be subjected to calcination with or without previous filtration in a conventional manner before admixing with the other ingredients of the catalyst, although this is unnecessary. And, if calcination is done it is preferably accomplished under conditions insufficient to cause significant crystallization. Furthermore, if the key catalytic phase is formed by techniques other than co-precipitation, such as, for example, metallurgical techniques, it can be combined with the other ingredients of the catalyst in the form derived.

It should also be appreciated that the order in which the various phases of the catalyst are added to one another is also not critical. More specifically, one or more components of the host-catalyst phase (either preformed or unpreformed) can be added to the key catalytic phase, or conversely the key catalytic phase can be added to one or more of the components (either preformed or unpreformed) of the host-catalyst phase. Furthermore, if all of the ingredients of the host-catalyst phase are not simultaneously combined with the key catalytic phase, the order in which the different elements of the host-catalyst phase are combined with the key catalytic phase is also unimportant.

The catalysts of the present invention are calcined prior to use. As is well known in the art, calcination of oxide complex catalysts serves to activate the catalysts, i.e. increase their catalytic activity. Also, calcination serves to drive off decomposable anions and cations which may be present in the pre-catalyst. In accordance with the present invention, calcination can be accomplished in the presence of oxygen, preferably air, or other gas in a conventional manner. For example, the catalyst can be calcined for a period of $\frac{1}{4}$ to 48 hours at temperatures of 200° to 800° C. in the presence of air.

The catalyst of the present invention may include significant amounts of essentially inert supports such as silica, alumina, alundum, pumice, titania, zirconia and the like. Such support materials are well known in the art for supporting oxide complex type catalysts, and any conventional support material can be employed in any conventional amount. When a support material is employed, it can be added to the remaining ingredients of the objective catalyst at any time and in any manner. For example, the support material can be added to the key catalytic phase prior to the addition of the host-catalyst phase or it can be added to the catalyst once formed before or even after a calcination. Preferably, however, the support material is added to the host-catalyst prior to combining the host-catalyst phase with the key catalytic phase.

As indicated above, an important feature of the present invention is that the key catalytic phase of the objective catalyst is preformed prior to admixing with other ingredients of the catalyst. Although not wishing to be bound in any theory, applicants believe that prior art processes for making molybdate and/or tungstate catalysts were disadvantageous because the element or elements M (e.g. Bi) had to compete with the other elements in the catalyst (e.g. Ni, Co or Fe) for molybdenum as the molybdate and/or tungstate species were formed. In accordance with the present invention, however, the M element is allowed to form a molybdate and/or tungstate without competition from competing elements so that the key catalytic phase can properly form. As a result, the catalysts produced by the inventive process have superior catalytic activity compared to catalysts produced by prior art techniques.

SPECIFIC EMBODIMENTS

In order to more thoroughly illustrate the present invention and its relation to the prior art, the following experiments are presented:

Comparative Example A

A catalyst of the formula:

50% $K_{0.1}Ni_{2.5}Co_{4.5}Fe_3BiP_{0.5}Mo_{12}O_x$ + 50% $SiO_2$ was prepared by a conventional catalyst preparation technique in the following manner:

36.36 g $FeNO_3.9H_2O$ was added to approximately 10 cc $H_2O$ and warmed by a hot plate until it dissolved/melted. Next, 14.55 g $BiNO_3.5H_2O$ was added to the solution and allowed to dissolve/melt therein. Thereafter 39.29 g $Co(NO_3)_2.6H_2O$ was added to the solution and allowed to dissolve/melt. Next, 21.81 g $Ni(NO_3)_2.6H_2O$ was added and allowed to dissolve/melt. Then 3.03 g of 10 weight percent $KNO_3$ aqueous solution was added to form a dark brown solution denoted as solution A.

In a separate container, 63.56 g $(NH_4)_6Mo_7O_{24}.4H_2O$ was dissolved in 65 cc $H_2O$ at 60° C. 205.49 g of a 40 percent silica sol (Nalco) was added to the dissolved ammonium heptamolybdate. Next 3.46 g of a 42 percent $H_3PO_4$ aqueous solution was added to form a slurry denoted as composition B.

Nitrate solution A was then slowly added with stirring to composition B and as a result a light yellow slurry was formed. The slurry was heated and stirred until it thickened. The thickened material was dried at 120° C. and then denitrified by heating in air at 290° C. for three hours followed by heating in air at 425° C. for three hours. The catalyst was then ground to 20 to 35 mesh size and the ground catalyst was calcined in air at 610° C. for three hours to yield the objective catalyst.

EXAMPLE 1

A catalyst having the following chemical formula was prepared by the process of the present invention:

50% $[Bi_2Mo_3O_{12}]_{\frac{1}{2}}$
$[K_{0.1}Ni_{2.5}Co_{4.5}Fe_3P_{0.5}Mo_{10.5}O_x]$ + 50% $SiO_2$ As will be noted, the chemical composition of this catalyst is identical to the chemical composition of the catalyst made in Comparative Example A.

14.55 g $Bi(NO_3)_3.5H_2O$ was dissolved in 100 ml. of a 10 percent $HNO_3$ aqueous solution. 7.95 g of $(NH_4)Mo_7O_{24}.4H_2O$ was dissolved in 100 ml. $H_2O$ with heating. The bismuth nitrate solution was then slowly added to the ammonium heptamolybdate solution with constant stirring. The pH was then adjusted to 2.5 to 3 by the addition of $NH_4OH$. The mixture was stirred for about one hour, thereby yielding a bismuth molybdate slurry.

In a separate container, 3.03 g of a 10 percent $KNO_3$ aqueous solution, 21.81 g $Ni(NO_3)_2.6H_2O$, 39.29 g $Co(NO_3)_2.6H_2O$ and 36.36 g $Fe(NO_3)_3.N.9H_2O$ were added to 50 ml. of water with heating. Next 55.61 g $(NH_4)_6Mo_7O_{24}.4H_2O$ was dissolved in 150 ml. of water with heating and to this solution was added 3.46 g of a 42.5 percent aqueous solution of $H_3PO_4$ and 205.49 g of a 40 percent silica sol (Nalco). Next, the metal nitrate solution was added to the ammonium heptamolybdate/phosphoric acid silica slurry and the mixture obtained stirred for one to two hours at 90° C. to form a host-catalyst slurry.

The previously prepared bismuth molybdate slurry was then added to the host-catalyst slurry with stirring. The mixture obtained was evaporated to dryness with constant sitrring on a hot plate and finally in a drying oven at 120° C. The dried material was then calcined in air at 290° C. for three hours, then 425° C. for three hours, then ground and screened to 20 to 35 mesh particle size. The ground material was then finally calcined at 610° C. for a period of three hours to yield the objective catalyst.

EXAMPLE 2

Example 1 was repeated except that the bismuth molybdate slurry was filtered to remove the preformed bismuth molybdate from the mother liquor. The bismuth molybdate was then dried overnight, calcined in the air at 290° C. for one hour and ball milled before being added to the host-catalyst slurry.

In order to compare the catalytic properties of the catalysts produced above, a series of experiments was conducted in which propylene was ammoxidized to acrylonitrile. In these experiments, 5 cc of each of the above catalysts was individually charged into a plug flow micro-reactor and a feed comprising 1.80 propylene/2.20 $NH_3$/2.94 air/2.88 $O_2$/5.89 $H_2O$ was fed to the reactor. The reaction temperature was maintained at 430° C. and the feed was fed to the reactor such that the contact time of the reaction was 6 seconds. The results obtained are set forth in the following table I. In this and following tables, yield is defined as:

$$\% \text{ yield} = \frac{\text{moles product produced}}{\text{moles propylene fed}}$$

TABLE I

| Catalyst | $NH_3$ burned | Acrylonitrile yield | HCN yield |
|---|---|---|---|
| Comp (A) | 16.4 | 72.7 | 2.8 |
| Ex. 1 | 9.0 | 78.0 | 4.6 |
| Ex. 2 | 11.9 | 75.8 | 2.8 |

From the foregoing table, it can be seen that the yield of the desired product, acrylonitrile, as well as useful byproduct HCN undergo a significant increase when the catalyst is produced in accordance with the inventive process. It will also be noted that the amount of $NH_3$ burnt is significantly reduced, which means significantly less $NH_3$ is wasted through the formation of $N_2$. And since the amount of ammonia burnt when using molybdate and tungstate catalysts in ammoxidation reactions tends to decrease with time, even greater ammonia savings can be expected than exemplified above. These advantages as well as the fact that inventive process is simple and easy to carry out make the present invention of significant commercial importance.

In order to further compare the catalytic properties of the catalysts produced by the present invention with prior art catalysts, two additional experiments involving the oxidation of propylene to acrolein and acrylic acid were conducted. In these experiments, 5 cc each of the catalysts of Example 1 and Comparative Example A were separately changed into a 5 cc flug flow, fixed-bed reactor. A feed comprising 1 propylene/11 air/4$H_2O$ was fed to the reactor in each test at a temperature of 350° C. and a contact time of 3 seconds. The results obtained are set forth in the following Table II.

TABLE II

| Catalyst | Acrolein yield | Acrylic acid yield | Sum of Acrolein & acrylic acid yields |
|---|---|---|---|
| Comp (A) | 78.3 | 3.8 | 82.1 |

| Catalyst | Acrolein yield | Acrylic acid yield | Sum of Acrolein & acrylic acid yields |
|---|---|---|---|
| Example 1 | 78.3 | 8.1 | 86.4 |

As can be seen, the yield of acrylic acid significantly increase when a catalyst of the present invention is used.

Although only a few specific embodiments of the present invention have been discussed above, it should be appreciated that many modifications can be made without departing from the spirit and scope of the invention. All such modifications are intended to be included within the scope of the present invention, which is limited only by the following claims:

We claim:

1. In a process for producing a molybdate or tungstate oxide complex catalyst in which compounds capable of yielding said catalyst are combined together so as to form a pre-catalyst solid and the pre-catalyst solid is calcined in air to activate said pre-catalyst and thereby form said catalyst, the improvement wherein the key catalytic phase of said catalyst comprising a molybdate and/or tungstate of Bi, Te, Sb, Sn, Cu or mixtures thereof is pre-formed prior to combining with the other elements in said catalyst; and further wherein none of the Group VIII elements in said catalyst, if any, is separately preformed into a molybdate or tungstate prior to combining with the key catalyst phase, said catalyst having a composition defined by the formula:

$$[M_mN_nO_x]_q [A_aC_bD_cE_dF_eN_fO_y]_p$$

wherein
M=Bi, Te, Sb, Sn and/or Cu
N=Mo and/or W
A=alkali, Tl, and/or Sm
C=Ni, Co, Mn, Mg, Be, Ca, Sr, Ba, Zn, Cd and/or Hg
D=Fe, Cr, Ce, and/or V
E=P, As, B, Sb
F=rare earth, Ti, Zr, Nb, Ta, Re, Ru, Rh Ag, Au, Al, Ga, In, Si, Ge, Pb, Th, and/or U, and further
wherein
a=0-4
b=0-20
c=0.01-20
d=0-4
e=0-8
f=8-16
m=0.01-10
n=0.1-30, and
x and y are numbers such that the valence requirements of the other elements for oxygen in the key catalytic phase and the host-catalyst phase, respectively, are satisfied; and the ratio q/p is 0.1 to 10.

2. The process of claim 1 wherein said key catalytic phase is a bismuth molybdate.

3. The process of claim 2 wherein said key catalytic phase is made by coprecipitation to form an aqueous slurry.

4. The process of claim 3 wherein the Bi/Mo ratio in said slurry is 9:1 to 1:9.

5. The process of claim 4 wherein said Bi/Mo ratio is 2:1 to 1:3.

6. The process of claim 5 wherein said Bi/Mo ratio is 2:1 to 2:3.

7. The process of claim 4 wherein the elements constituting said catalyst other than the elements in said key catalytic phase constitute a host-catalyst phase, said host-catalyst phase being preformed in an aqueous slurry prior to admixing with said pre-catalyst phase.

8. The process of claim 7 wherein said preformed host-catalyst phase is added to the key catalytic phase slurry without filtering said key catalytic phase slurry.

9. The process of claim 4 wherein the elements constituting said catalyst other than elements in said key catalytic phase constitute a host-catalyst phase, the compounds capable of yielding the elements of said host-catalyst phase being individually added to the key catalytic phase aqueous slurry.

10. The process of claim 1 where substantially all of the Bi, Te, Sb, Sn, Cu or mixture thereof in said catalysts is formed into said key catalytic phase.

11. The process of claim 1 wherein said key catalytic phase is combined with the other elements of said catalyst prior to heating of said key catalytic phase to calcination.

12. The process of claim 1 wherein said catalyst contains a Group VIII metal.

13. The process of claim 1 wherein the portion of said formula denoted as $$[M_mN_nO_x]_q$$

constitutes said key catalytic phase.

* * * * *